(12) United States Patent
Kashiwagi et al.

(10) Patent No.: US 8,581,932 B2
(45) Date of Patent: Nov. 12, 2013

(54) IMAGE DISPLAY SYSTEM

(75) Inventors: Nobuhiko Kashiwagi, Kanagawa (JP); Ayako Muramoto, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 355 days.

(21) Appl. No.: 12/929,521

(22) Filed: Jan. 31, 2011

(65) Prior Publication Data
US 2011/0242092 A1 Oct. 6, 2011

(30) Foreign Application Priority Data
Mar. 30, 2010 (JP) ................. 2010-079516

(51) Int. Cl.
G09G 5/00 (2006.01)
G06K 9/00 (2006.01)
G06K 9/32 (2006.01)

(52) U.S. Cl.
USPC ............... 345/629; 382/128; 382/294

(58) Field of Classification Search
USPC .................. 345/629; 382/128, 284
See application file for complete search history.

(56) References Cited

U.S. PATENT DOCUMENTS 7,577,282 B2 * 8/2009 Gkanatsios et al. .......... 382/128
7,616,801 B2 * 11/2009 Gkanatsios et al. .......... 382/132
7,916,915 B2 * 3/2011 Gkanatsios et al. .......... 382/128
8,150,132 B2 * 4/2012 Nakamura .................... 382/131
8,194,947 B2 * 6/2012 Zingaretti et al. ............ 382/128
8,294,733 B2 * 10/2012 Eino .............................. 345/629
8,345,957 B2 * 1/2013 Sakaguchi .................... 382/154
2004/0057600 A1 * 3/2004 Niwa ............................. 382/103
2006/0098855 A1 * 5/2006 Gkanatsios et al. .......... 382/128
2007/0248210 A1 * 10/2007 Selse et al. ...................... 378/37
2007/0274585 A1 * 11/2007 Zhang et al. .................. 382/132
2008/0118138 A1 * 5/2008 Zingaretti et al. ............ 382/132
2009/0141859 A1 * 6/2009 Gkanatsios et al. ............ 378/37
2009/0296882 A1 * 12/2009 Gkanatsios et al. ............ 378/37

FOREIGN PATENT DOCUMENTS

| JP | 2007-050264 | 3/2007 |
| JP | 2007-325796 | 12/2007 |
| JP | 2008-067933 | 3/2008 |

* cited by examiner

*Primary Examiner* — M Good Johnson
(74) *Attorney, Agent, or Firm* — Jean C. Edwards; Edwards Neils PLLC

(57) ABSTRACT

An image display system including: an image acquisition section that acquires a specific number of images of an imaging subject by imaging with an imaging section from different respective imaging positions; a detection section that detects regions of attention expressing specific loci of attention in each of the specific number of images acquired by the image acquisition section; and a selection section that selects, from combinations of the images, a combination of images for display as images on a display section, the combination of images having a minimum number of images having all of the loci of attention expressed by the regions of attention detected by the detection section in the specific number of images.

5 Claims, 15 Drawing Sheets

| LOCUS OF ATTENTION \ IMAGE | 1st IMAGE | 2nd IMAGE | Mth IMAGE | N-1th IMAGE | Nth IMAGE |
|---|---|---|---|---|---|
| A | PRESENT | PRESENT | ABSENT | ABSENT | ABSENT |
| B | PRESENT | PRESENT | ABSENT | ABSENT | ABSENT |
| C | ABSENT | ABSENT | PRESENT | ABSENT | ABSENT |
| D | ABSENT | ABSENT | PRESENT | ABSENT | ABSENT |
| E | ABSENT | ABSENT | PRESENT | ABSENT | ABSENT |
| F | ABSENT | ABSENT | PRESENT | ABSENT | ABSENT |
| G | ABSENT | ABSENT | ABSENT | PRESENT | ABSENT |
| H | ABSENT | ABSENT | ABSENT | PRESENT | PRESENT |

LEFT-RIGHT DIRECTION

FIG. 7
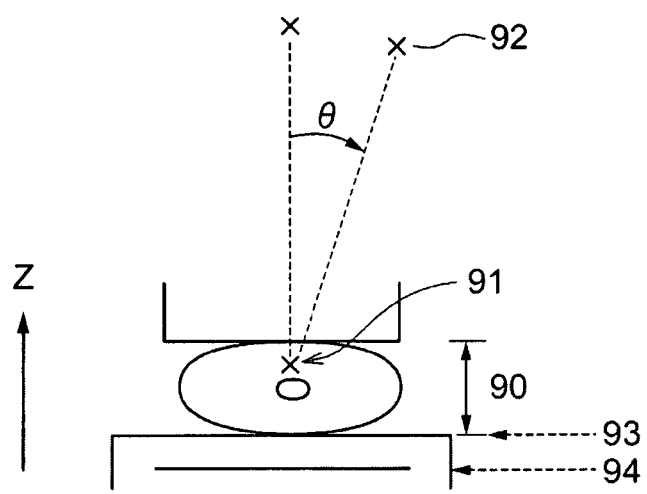
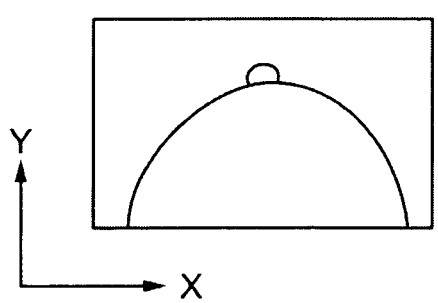

FIG. 9

| LOCUS OF ATTENTION / IMAGE | 1st IMAGE | 2nd IMAGE | Mth IMAGE | N-1th IMAGE | Nth IMAGE |
|---|---|---|---|---|---|
| A | PRESENT | PRESENT | ABSENT | ABSENT | ABSENT |
| B | PRESENT | PRESENT | ABSENT | ABSENT | ABSENT |
| C | ABSENT | ABSENT | PRESENT | ABSENT | ABSENT |
| D | ABSENT | ABSENT | PRESENT | ABSENT | ABSENT |
| E | ABSENT | ABSENT | PRESENT | ABSENT | ABSENT |
| F | ABSENT | ABSENT | ABSENT | ABSENT | ABSENT |
| G | ABSENT | ABSENT | ABSENT | PRESENT | ABSENT |
| H | ABSENT | ABSENT | ABSENT | PRESENT | PRESENT |

99

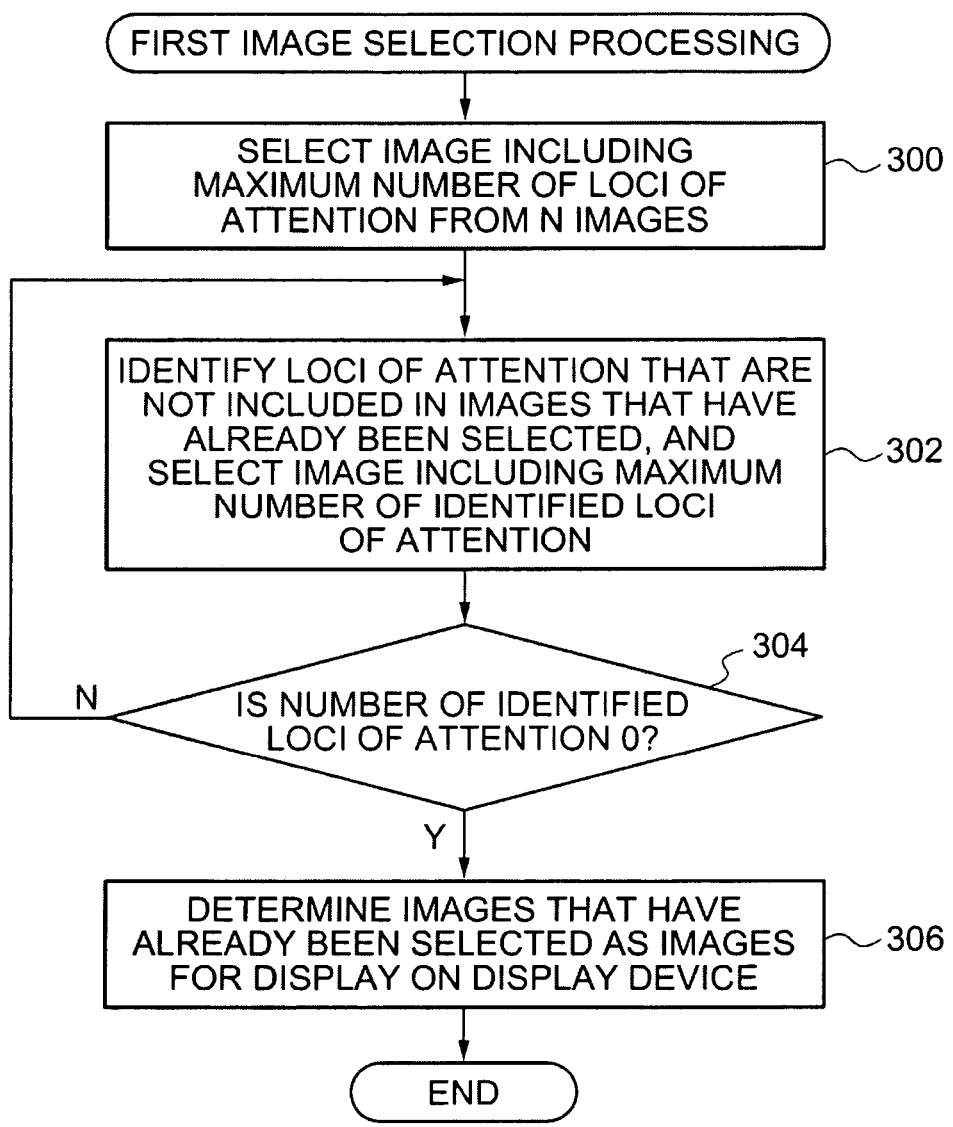

FIG. 16

| LOCUS OF ATTENTION \ IMAGE | 1st IMAGE | 2nd IMAGE | Mth IMAGE | M+1th IMAGE | N-1th IMAGE | Nth IMAGE |
|---|---|---|---|---|---|---|
| A | PRESENT | PRESENT | ABSENT | ABSENT | ABSENT | ABSENT |
| B | PRESENT | PRESENT | ABSENT | ABSENT | ABSENT | ABSENT |
| C | ABSENT | ABSENT | PRESENT | PRESENT | ABSENT | ABSENT |
| D | ABSENT | ABSENT | PRESENT | PRESENT | ABSENT | ABSENT |
| E | ABSENT | ABSENT | PRESENT | PRESENT | ABSENT | ABSENT |
| F | ABSENT | ABSENT | ABSENT | ABSENT | ABSENT | ABSENT |
| G | ABSENT | ABSENT | ABSENT | ABSENT | PRESENT | PRESENT |
| H | ABSENT | ABSENT | ABSENT | ABSENT | PRESENT | PRESENT |

99'

IMAGE DISPLAY SYSTEM

CROSS-REFERENCE TO RELATED APPLICATION

This application claims priority under 35 USC 119 from Japanese Patent Application No. 2010-079516, filed on Mar. 30, 2010, the disclosure of which is incorporated by reference herein.

BACKGROUND

1. Technical Field

The present invention relates to an image display system.

2. Related Art

There are previously known radiographic imaging devices (imaging devices) that perform radiographic imaging for the purpose of medical diagnostics. For such types of radiographic imaging device, there is, for example, a known technique for performing tomosynthesis imaging to image a breast of an investigation subject from plural angles, for purposes such as early diagnosis of breast cancer.

The slice images acquired of the breast by tomosynthesis imaging with images acquired from plural angles are particularly effective for highly dense (with many mammary glands) breasts (known as dense breasts). An example of the reason for this is that during imaging from one angle the transmission rate of mammary glands is low, and so although there is a risk of misdiagnosis if, for example, a tumor does not show up on an image due to the presence of mammary glands masking the tumor, the tumor becomes more readily picked up in the images by imaging from plural angles.

There are also known 3-dimensional viewing systems by which the breast can be viewed at a whole all at once.

However, the display of slice images only provides fragmentary data, and for a 3-dimensional image, consideration needs to be given to a combination made from the slice images, with the possibility of this leading to a tumor being overlooked. It is also necessary to check all of the plural slice images, with the possibility that this leads to the time for interpretation being longer than previously.

In a 3-dimensional system, there is an advantage as a tool by which the breast can be envisaged all at once, however, since the data amount for displaying the breast as a whole is based on data from two images taken from a limited angular field of view of about 4 to 10 degrees, the amount of data is not sufficient in comparison to the amount of data obtained from the great number of images acquired by tomosynthesis imaging, and in particular it is not sufficient to find tumors and the like in dense breasts.

Note that while there is a technique to detect regions of interest by computer aided detection (CAD) as a means to shorten the duration for interpreting slice images obtained by tomosynthesis imaging, in order to reach an opinion, a 3-dimensional image of the breast must be considered, and this takes time for interpretation. The regions of interest, for example, refer to regions of attention expressing loci of attention on the images. An example of a locus of attention is a calcified location.

SUMMARY

The present invention is made in consideration of the above circumstances, and provides an image display system with which efficient interpretation can be made, and can suppress loci of attention from being overlooked.

An image display system of a first aspect of the present invention includes: an image acquisition section that acquires a specific number of images of an imaging subject by imaging with an imaging section from different respective imaging positions; a detection section that detects regions of attention expressing specific loci of attention in each of the specific number of images acquired by the image acquisition section; and a selection section that selects, from combinations of the images, a combination of images for display as images on a display section, the combination of images having a minimum number of images having all of the loci of attention expressed by the regions of attention detected by the detection section in the specific number of images.

According to the image display system of the first aspect of the present invention, the combination of images having the minimum number of images having all of the loci of attention expressed by the detected regions of attention in the specific number of images is selected from the combinations of the images by the selection section for display as images on the display section. Accordingly, since the minimum number of images are displayed in order to display all of the loci of attention, efficient interpretation can be made, while suppressing loci of attention from being overlooked.

An image display system of a second aspect of the present invention is the first aspect of the present invention, further including: an association application section that, between the images, applies associations to regions of attention that express a same locus of attention, based on an imaging position of the imaging section in each of the specific number of images and a position of the region of attention detected in each of the images; and wherein, the selection section selects, from the combinations of the images, the combination of images for display as images on the display section, the combination of images having the minimum number of images having all of the loci of attention expressed by the regions of attention detected by the detection section in the specific number of images, based on the associations applied by the association application section to the regions of attention expressing the same locus of attention.

An image display system of a third aspect of the present invention includes: an image acquisition section that acquires a specific number of images of an imaging subject by imaging with an imaging section from different respective imaging positions; a detection section that detects regions of attention expressing specific loci of attention in each of the specific number of images acquired by the image acquisition section; and a selection section that, in cases where there are a plurality of sets of image pairs determined, the image pair being a single set of two images in the specific number of images imaged by the imaging section, selects, from combinations of the image pairs, a combination of image pairs for display as images on a display section, the combination of image pairs having a minimum number of the image pairs having all of the loci of attention expressed by the regions of attention detected by the detection section in the specific number of images.

According to the image display system of the third aspect of the present invention, cases where there are plural sets of image pairs determined, each image pair being a single set of two images, the selection section selects, from combinations of the image pairs, the combination of images for display as images on a display section, the combination of image pairs having the minimum number of the image pairs having all of the loci of attention expressed by the regions of attention detected in the specific number of images. Accordingly, since the minimum number of images are displayed in order to display all of the loci of attention, efficient interpretation can be made, while suppressing loci of attention from being overlooked.

An image display system of a fourth aspect of the present invention is the third aspect of the present invention that may be configured further including: an association application section that, between the images, applies associations to regions of attention that express a same locus of attention, based on an imaging position of the imaging section in each of the specific number of images and a position of the region of attention detected in each of the images; and wherein, the selection section selects, from the combinations of the image pairs, the combination of image pairs for display as images on the display section, the combination of image pairs having the minimum number of the image pairs having all of the loci of attention expressed by the regions of attention detected by the detection section in the specific number of images, based on the associations applied by the association application section to the regions of attention expressing the same locus of attention.

An image display system of a fifth aspect of the present invention is the third aspect of the present invention that may be configured such that: each of the image pairs is two images acquired by imaging with the imaging section at different imaging positions that are at a specific parallactic angle to each other; and the display section displays images of each of the image pairs in the selected combination as a three-dimensional image.

According to the image display system of the fifth aspect of the present invention, time is saved when considering the three dimensional image of the breast N as a whole, and even more efficient interpretation can be made, while suppressing regions of interest being overlooked.

BRIEF DESCRIPTION OF THE DRAWINGS

Exemplary embodiments of the present invention will be described in detail based on the following figures, wherein:

FIG. 7 is an explanatory diagram of chart generation processing;

FIG. 9 is a schematic diagram of a generated chart;

FIG. 10 is a flow chart showing a first image selection processing flow according to the first exemplary embodiment;

FIG. 16 is a schematic diagram of a generated chart.

DETAILED DESCRIPTION

Explanation follows, with reference to the drawings, regarding examples in which the present invention is applied to a radiographic imaging device (imaging device) capable of imaging an imaging subject from different respective imaging positions.

First Exemplary Embodiment

Figure 1:
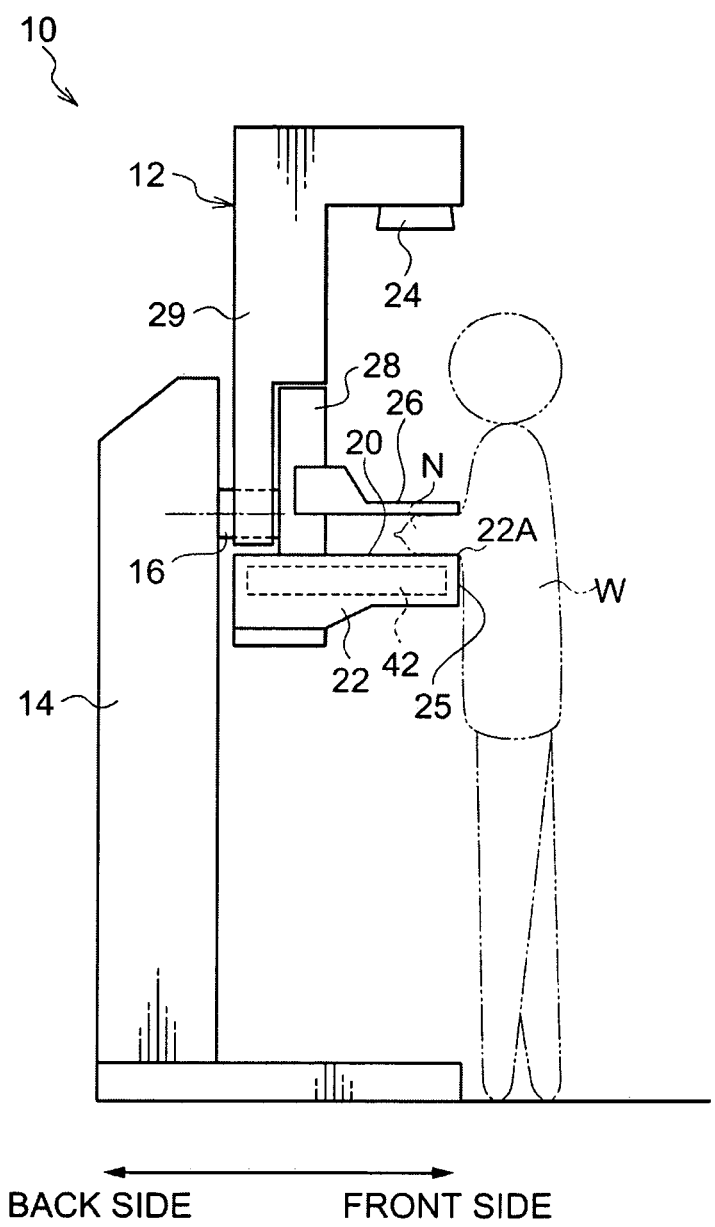
FIG. 1 is a plan view showing a configuration of a radiographic imaging device according to a first exemplary embodiment.
Figure 2:
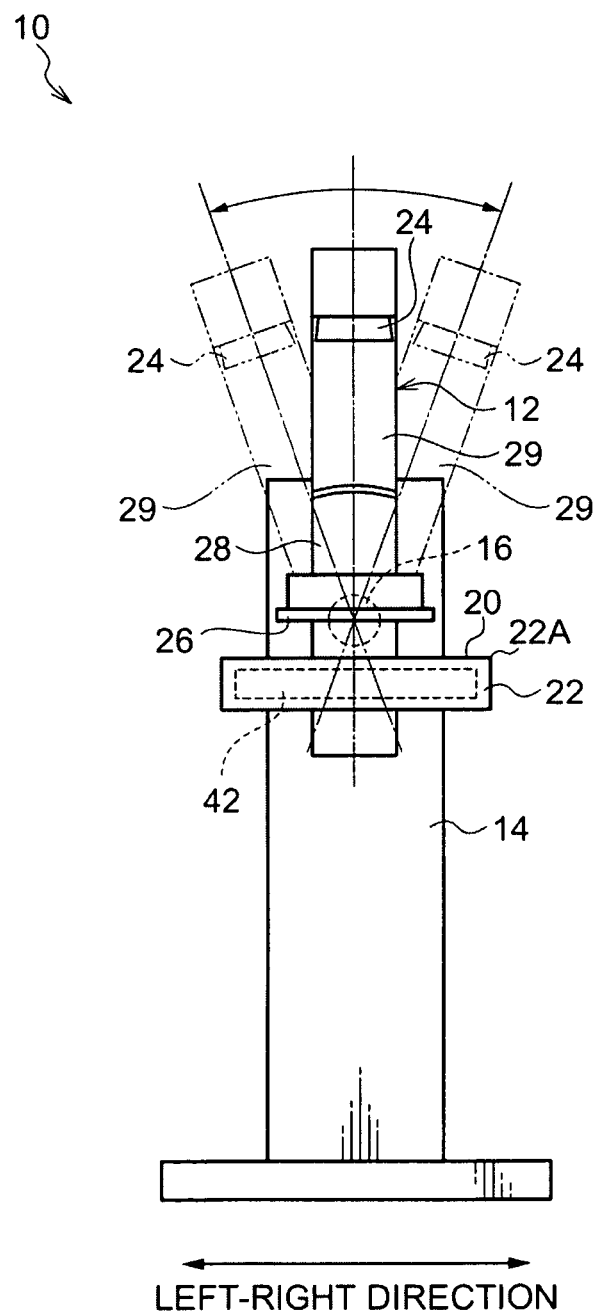
FIG. 2 is a diagram showing a configuration during imaging with a radiographic imaging device according to the first exemplary embodiment.

Explanation first follows regarding a first exemplary embodiment. As shown in FIG. 1 to FIG. 2, a radiographic imaging device 10 according to the present exemplary embodiment is a device for imaging a breast N of an investigation subject W using radiation (for example, X-rays) while the investigation subject W is in an upright state, referred to, for example, as mammography. In the explanation that follows, the near side in the vicinity of the investigation subject W when the investigation subject W faces the radiographic imaging device 10 during imaging is referred to as the device front side of the radiographic imaging device 10, the far side away from the investigation subject W when the investigation subject W faces the radiographic imaging device 10 is referred to as the device back side of the radiographic imaging device 10, and the left-right direction of the investigation subject W when the investigation subject W faces the radiographic imaging device 10 is referred to as the device left-right direction of the radiographic imaging device 10 (see each of the arrows on FIG. 1 and on FIG. 2).

The imaging subject as the imaging subject of the radiographic imaging device 10 is not limited to the breast N, and, for example, application may be made to other locations of the body or other objects. As the radiographic imaging device 10, as long as it is an device in which the breast N of an investigation subject W is imaged with at least the upper body of the investigation subject W in an upright state, application may be made to a device for imaging the breast N of an investigation subject W with the investigation subject W in a seated state on a seat or the like.

The radiographic imaging device 10, as shown in FIG. 1, is equipped with a measurement section 12 that is substantially C-shape in side view and is provided at the device front side, and a base section 14 that supports the measurement section 12 from the device back side.

The measurement section 12 is equipped with: an object table 22 formed with a flat plane shaped imaging face 20 that makes contact with the breast N of the investigation subject W who is in an upright state; a press plate 26 for pressing the breast N between the press plate 26 and the imaging face 20 of the object table 22; and a holding section 28 that holds the object table 22 and the press plate 26. Note that a substance is used for the press plate 26 that is transparent to radiation.

The measurement section 12 is equipped with: a radiation irradiation section 24 provided with a radiation source 30 such as a tube (see FIG. 4) for irradiating investigation radiation from the radiation source 30 towards the imaging face 20; and a support section 29 that supports the radiation irradiation section 24 separated from the holding section 28.

A rotation shaft 16 is provided to the measurement section 12, rotatably supported from the base section 14. The rotation shaft 16 is fixed relative to the support section 29, such that the rotation shaft 16 and the support section 29 rotate as one.

The holding section 28 is switchable between a state in which it is coupled to the rotation shaft 16 and rotates as one therewith, and a state in which the rotation shaft 16 is separated in a free-wheeling state. Specifically, the rotation shaft 16 and the holding section 28 are respectively provided with gears, and these gears can be switched between a meshed state of the gears with each other, and an unmeshed state.

Note that various mechanical elements can be employed in order to switch between transmitting and not transmitting rotation force of the rotation shaft 16.

The holding section 28 holds the object table 22 and the radiation irradiation section 24 such that the imaging face 20 and the radiation irradiation section 24 are separated by a specific separation. The holding section 28 also holds the press plate 26 such that the press plate 26 is capable of sliding movement, thereby enabling change to the separation between the press plate 26 and the imaging face 20.

From the standpoints of radiation transmissivity and strength, the imaging face 20 that contacts the breast N is formed, for example, from a carbon composite. A radiation detector 42 is disposed inside the object table 22, and the radiation detector 42 is irradiated with radiation that has passed through the breast N and the imaging face 20 and detects this radiation. The radiation detected by the radiation detector 42 is made visible and a radiographic image is generated. Namely, a radiographic image can be acquired by the radiation detector 42. The radiation irradiation section 24 and the radiation detector 42 correspond, respectively, to an imaging section and an image acquisition section.

Figure 3:
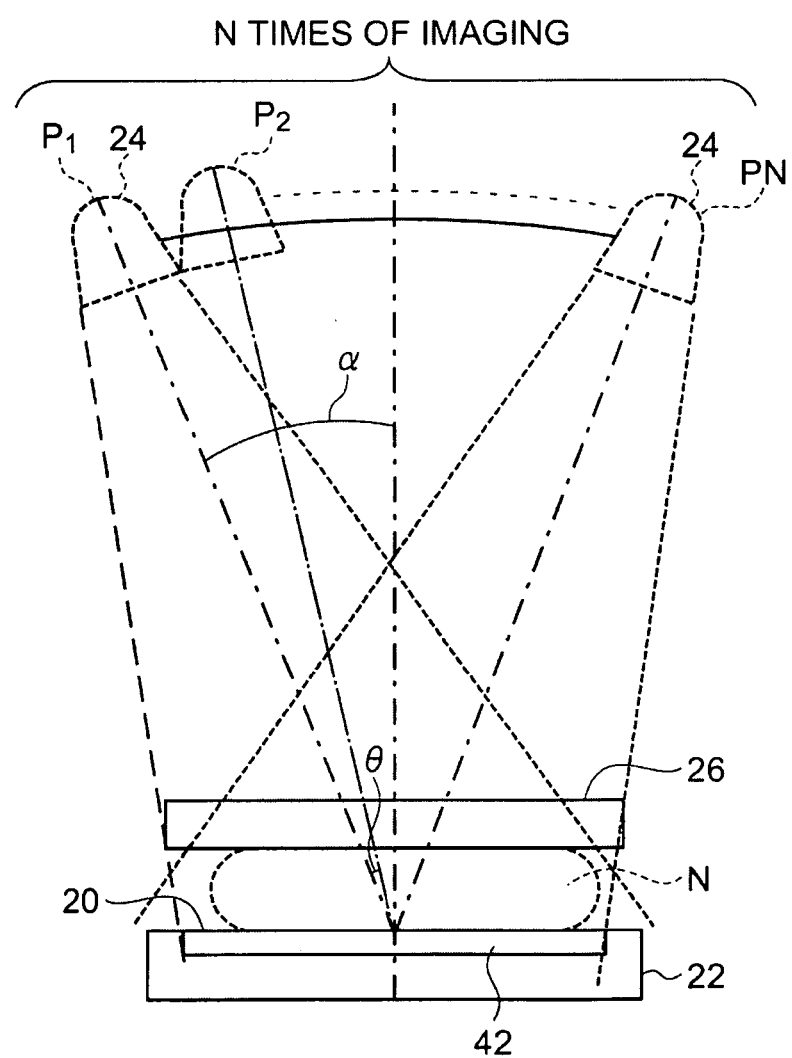
FIG. 3 is an explanatory diagram during imaging with a radiographic imaging device according to the first exemplary embodiment.

The radiographic imaging device 10 according to the present exemplary embodiment is a device that can at least perform imaging of a breast N as the imaging subject from plural directions. FIG. 2 and FIG. 3 show respective orientations of the radiographic imaging device 10 during imaging, and positions of the radiation irradiation section 24 during imaging. As shown in FIG. 2 and FIG. 3, such imaging is performed with the support section 29 that supports the radiation irradiation section 24 inclined relative to the object table 22 that is supported through the holding section 28.

In the radiographic imaging device 10, as shown in FIG. 3, in order to perform imaging on the breast N from plural directions, the radiation irradiation section 24 alone is moved in a circular arc shape by rotating the support section 29, without moving the object table 22 and the press plate 26, by making the rotation shaft 16 rotate relative to the holding section 28. Note that in the present exemplary embodiment, as shown in FIG. 3, the imaging position is moved by specific angles θ at a time from an angle α, thereby performing imaging with the position of the radiation irradiation section 24 at N locations, $P_1$ to $P_N$.

Rotating the radiation irradiation section 24 alone in this manner enables the radiation irradiation section 24 to be positioned at plural positions.

The radiation irradiation section 24 according to the present exemplary embodiment has plural of the radiation sources 30 installed therein, and it is possible to selectively switch between the radiation source 30 to be employed by using a switching mechanism.

A Chest wall face 25 is formed at the face of the object table 22 on the device front side, and a chest portion of the investigation subject W below the breast N makes contact with the chest wall face 25 during imaging. The chest wall face 25 is formed in a flat face shape.

Figure 4:
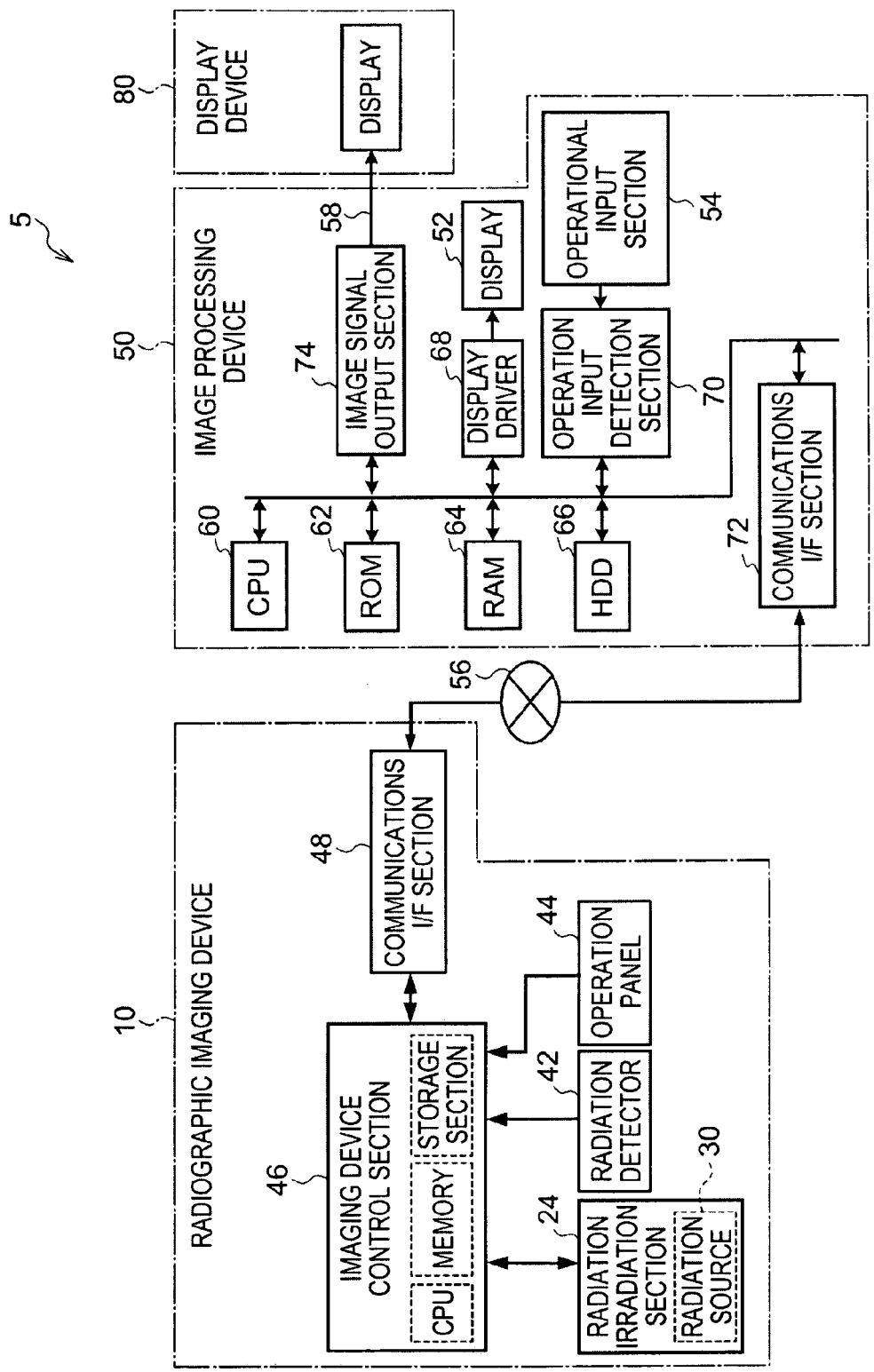
FIG. 4 is a block diagram showing a configuration of a radiographic imaging system according to the first exemplary embodiment.

FIG. 4 shows a block diagram with a detailed configuration of a radiographic image display system 5 according to the present exemplary embodiment.

The radiographic image display system 5 is equipped with: the radiographic imaging device 10 as described above; an image processing device 50 that performs specific image processing such as on the imaged radiographic image, such as shading correction, first display control processing, described in detail below, chart generation processing, image selection processing, or the like; and a display device 80 that displays an image to which specific image processing has been performed by the image processing device 50.

The radiographic imaging device 10 is equipped with: the radiation detector 42; an operation panel 44 for inputting various operational data, such as imaging conditions, orientation data, and the like, and various operational instructions; an imaging device control section 46 that controls the operation of the device as a whole; and a communications I/F section 48 that is connected to a network 56, such as a LAN, and transmits and receives various data to and from other devices connected to the network 56.

The imaging device control section 46 is equipped with a Central Processor Unit (CPU), a memory, including Read Only Memory (ROM) and Random Access Memory (RAM), and a non-volatile storage section (storage means) formed by a Hard Disk Drive (HDD) and/or flash memory. The imaging device control section 46 is connected to the radiation irradiation section 24, the radiation detector 42, the operation panel 44 and the communications I/F section 48.

Imaging conditions instructed by the operation panel 44 include data for tube voltage, tube current, irradiation duration and the like. Orientation data includes data expressing the imaging position (imaging orientation, angle) for performing imaging of the breast N from plural directions. Configuration may be made such that the various operational data, such as imaging conditions, orientation data, and the like, and various operational instructions is obtained from another control device.

In order to perform imaging from plural directions, the imaging device control section 46 adjusts the orientation of the holding section 28 to a state in which the imaging face 20 faces upwards, and also adjusts the orientation of the support section 29 to a state such that the radiation irradiation section 24 is positioned above the imaging face 20. Then, as shown in FIG. 3, the imaging device control section 46 rotates the support section 29 so as to move the radiation irradiation section 24 in steps of angle θ at a time in a circular arc shape from angle α, and, based on the imaging conditions, irradiates X-rays from the radiation source 30 provided to the radiation irradiation section 24 separately at different angles relative to the imaging face 20. N frames of radiographic images are thereby obtained.

The radiation detector 42 stores image data received from irradiation of radiation carrying the image data, and outputs the stored image data. The radiation detector 42 is configured, for example, as a Flat Panel Detector (FPD), disposed with a radiation sensitive layer that converts radiation into digital data and outputs the digital data. When radiation is irradiated onto the radiation detector 42, image data expressing the radiographic image that has been irradiated is output to the imaging device control section 46.

The imaging device control section 46 capable of communication with the image processing device 50 via the communications I/F section 48 and the network 56, and performs transmission and reception of various data to and from the image processing device 50.

The image processing device 50 is configured by a server computer, and is equipped with a display 52 that displays an operation menu, various data and the like, and an operational input section 54 configured including plural keys for inputting various data and operational instructions.

The image processing device 50 is equipped with: a CPU 60 for controlling the operation of the device overall; a ROM 62 pre-stored with various programs, including a control program, and the like; a RAM 64 for temporarily storing various data; an HDD 66 for storing and holding various data; a display driver 68 for controlling display of various data on the display 52; an operation input detection section 70 for detecting the operational state of the operational input section 54; a communications I/F section 72 that is connected to the radiographic imaging device 10 via the network 56 and performs transmission and reception of various data to and from the radiographic imaging device 10; and an image signal output section 74 that outputs an image signal to the display device 80 via a display cable 58.

The CPU 60, the ROM 62, the RAM 64, the HDD 66, the display driver 68, the operation input detection section 70, the communications I/F section 72, and the image signal output section 74 are mutually connected via a system bus. Accordingly, the CPU 60 can access the ROM 62, the RAM 64, and the HDD 66. The CPU 60 can also control display of various data on the display 52 via the display driver 68, control transmission and reception of various data to and from the radiographic imaging device 10 via the communications I/F section 72, and control the images for display on the display device 80 via the image signal output section 74. The CPU 60 also can ascertain the user operational state of the operational input section 54 via the operation input detection section 70.

The display device 80 displays an image on a display based on an input image signal.

Explanation now follows regarding operation of the radiographic image display system 5 according to the present exemplary embodiment.

In order to perform radiographic imaging, an imaging instruction, imaging conditions and orientation data is input to the operation panel 44 of the radiographic imaging device 10.

When input with an imaging instruction to perform imaging on the breast N from plural directions, the radiographic imaging device 10, as shown in FIG. 2, adjusts the orientation of the holding section 28 to a state in which the imaging face 20 faces upwards, and also adjusts the support section 29 to a state in which the radiation irradiation section 24 is positioned above the imaging face 20.

The investigation subject W contacts her breast N against the imaging face 20 of the radiographic imaging device 10. When operational instruction is performed in this state to the operation panel 44 to start pressing, the radiographic imaging device 10 moves the press plate 26 towards the imaging face 20. The press plate 26 contacts the breast N and further presses, and when the pressing force of the press plate 26 reaches a set pressing force, movement of the press plate 26 is stopped by control from the imaging device control section 46.

In the radiographic imaging device 10 according to the present exemplary embodiment, when an imaging instruction is input to the operation panel 44 in this operational state to perform imaging of the breast N from plural directions, the support section 29 alone is rotated, and the radiation irradiation section 24 is moved in a circular arc shape. As shown in FIG. 3, the imaging position of the radiation irradiation section 24 is moved from an angle α by a specific angle θ at a time, and radiation irradiation is performed based on the respective imaging conditions with the position of the radiation irradiation section 24 at N locations, $P_1$ to $P_N$. The radiation separately irradiated from the radiation irradiation section 24 reaches the radiation detector 42 after passing through the breast N.

When irradiated with radiation, the radiation detector 42 outputs respective image data expressing the irradiated radiographic images to the imaging device control section 46. As described above, when radiation irradiation is performed with the position of the radiation irradiation section 24 at N locations, $P_1$ to $P_N$, image data for N frames of images is output to the imaging device control section 46.

The imaging device control section 46 outputs the input image data to the image processing device 50. As described above, in cases where radiation irradiation is performed with the position of the radiation irradiation section 24 at N locations, $P_1$ to $P_N$, the CPU of the imaging device control section 46 outputs image data of the N frames of images to the image processing device 50 and also outputs to the image processing device 50 a specific instruction to execute the first display control processing.

The CPU 60 of the image processing device 50 first performs specific image processing, such as shading correction or the like, on the input image data, then controls the display device 80 so as to display the image on which the specific image processing has been performed.

Figure 5:
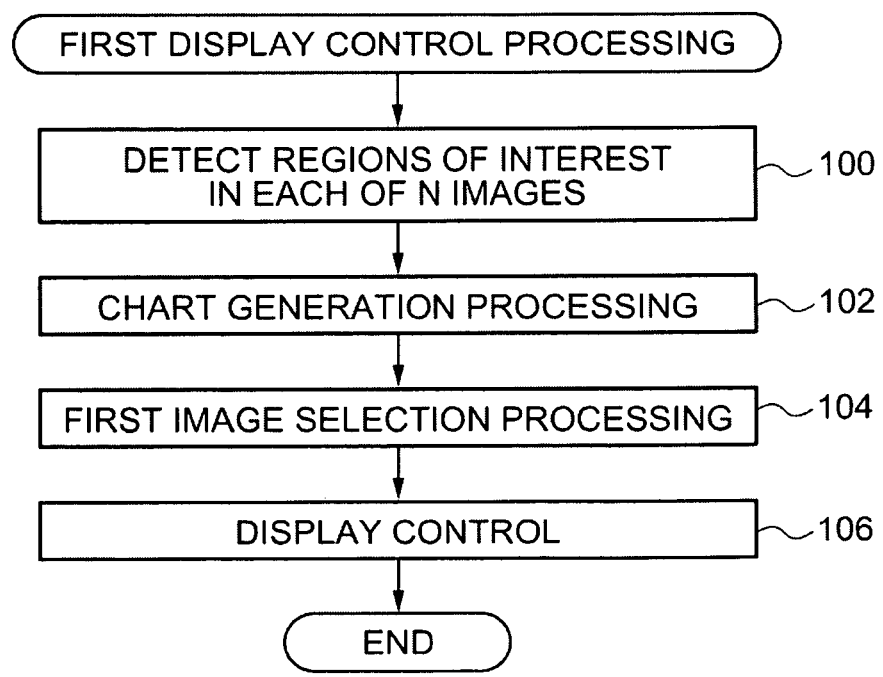
FIG. 5 is a flow chart showing a flow of first display control processing according to the first exemplary embodiment.

When in receipt of the above specific instruction, the CPU 60 of the image processing device 50 executes first display control processing as shown in FIG. 5. FIG. 5 shows a flow chart of the first display control processing flow of a first display control processing program executed by the CPU 60 when the specific instruction is received. This program is, for example, pre-stored in a specific region of the ROM 62.

First, at step 100, a region of interest (ROI) of the investigation subject is detected by computer aided detection (CAD) on each of the input N frames of images. The region of interest is thereby detected for each of the images. Note that the region of interest is a region of attention expressing a specific locus of attention on the image. For example, a calcified location is an example of a specific locus of attention, and indicates a calcified region on the image as the region of attention.

Figure 6:
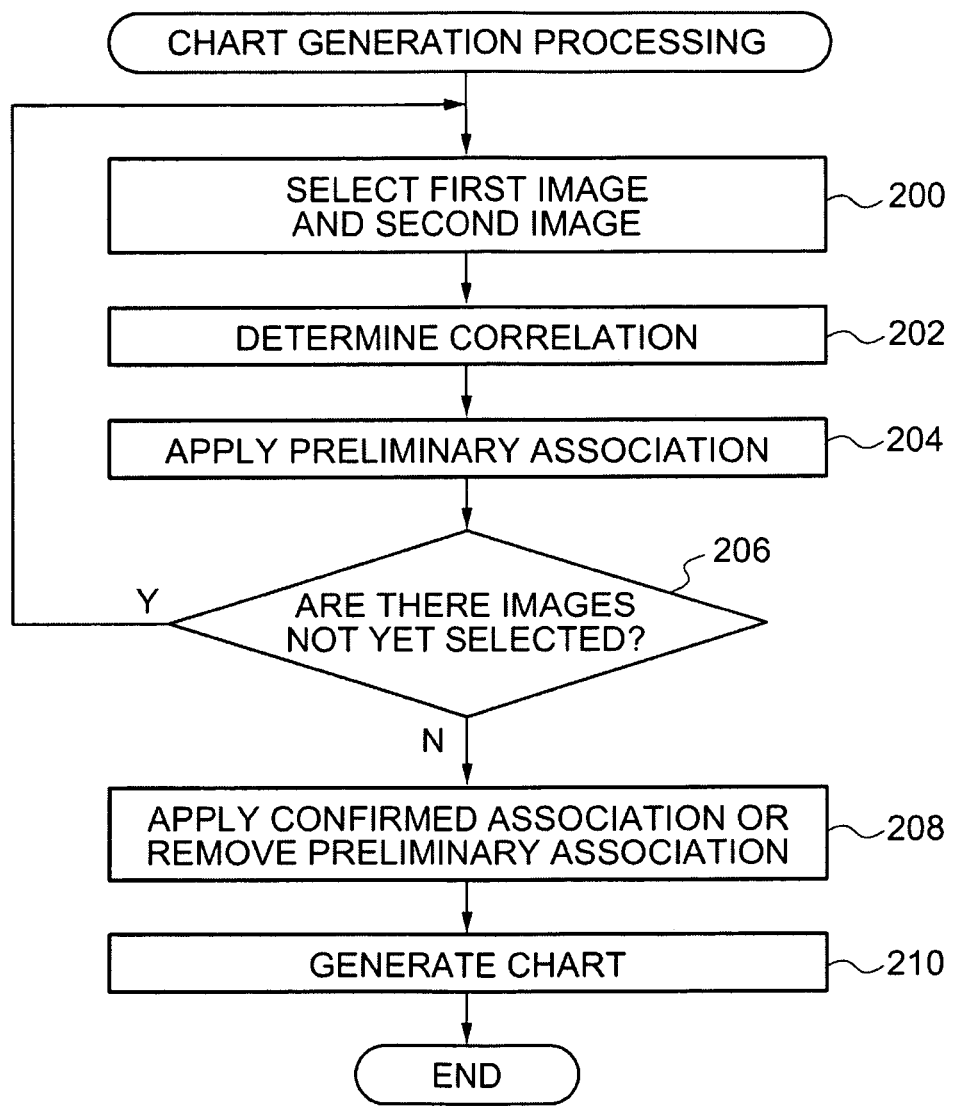
FIG. 6 is a flow chart showing a chart generation processing flow according to the first exemplary embodiment.

In the next step 102, chart generation processing is executed. FIG. 6 shows a flow chart of chart generation processing executed at step 102. Note that the chart generation processing described below is an example of processing for applying associations to the regions of attention on each of the images and recording a chart.

First, at step 200, the image (referred to below as the first image) obtained by radiation irradiation when the position of the radiation irradiation section 24 was at $P_k$ ($2 \leq K \leq N-2$) and the image (referred to below as the second image) obtained by radiation irradiation when the position of the radiation irradiation section 24 was at $P_{k+1}$ are selected.

Figure 8B:
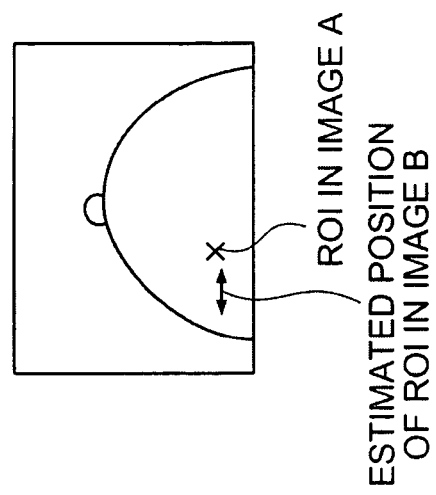
FIG. 8B is an explanatory diagram of chart generation processing.
Figure 8A:
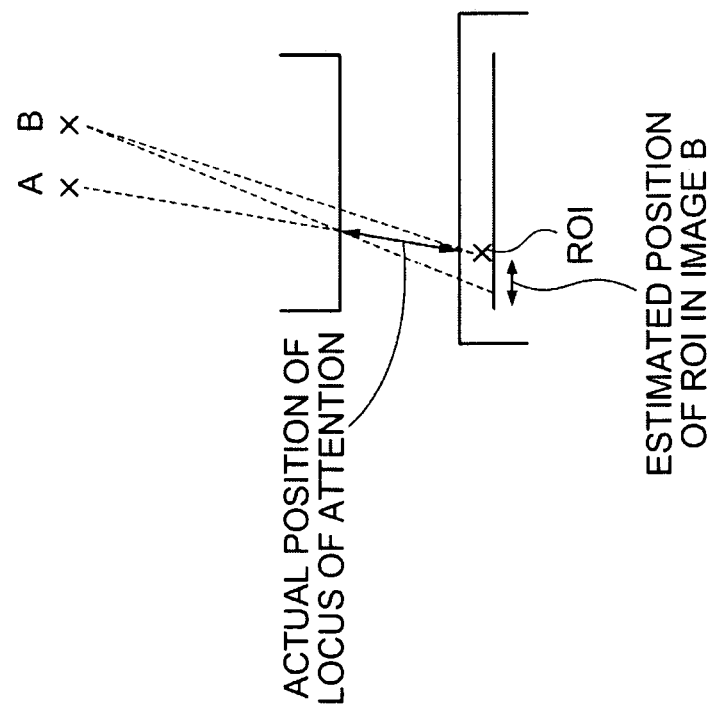
FIG. 8A is an explanatory diagram of chart generation processing.

Next, at step 202, paying attention to a given region of interest from the first image, as shown in FIG. 8A and FIG. 8B, the displacement in the X-direction on the second image from the position on the first image is estimated using: the angle formed between the imaging direction when imaging the first image and the imaging direction when imaging the second image, as shown in FIG. 7, (angle θ in the present exemplary embodiment) and the known positional relationship between a breast thickness 90 and a center of rotation position 91 of the radiation irradiation section 24, a source position 92 of the radiation source 30, a surface position 93 of the imaging face 20, and a position 94 of the radiation detector 42. Note that in the example shown in FIG. 8A and FIG. 8B, the range shown by the arrow from the region of interest to which attention is being paid on the first image is the range within which the region of interest to which attention is being paid is conceivably positioned on the second image. Determination is made as to whether or not the region of interest is present on the second image within this range. When determined that the region of interest is present, determination is made that the region of interest to which attention is being paid on the first image and the region of interest determined to be present on the second image "have correlation". Similar processing to that described above is then performed for a region of interest on the first image that has not yet been paid attention to (region of interest yet to be paid attention to), and the above processing is repeated until there are no longer any regions of interest yet to be paid attention to (namely, repeated for all of the regions of interest on the first image). Then, similar processing to the above is performed recursively for all the regions of interest on the second image. Note that a one-to-many relationship is sometimes obtained here for region(s) of interest of the first image and region(s) of interest of the second image.

In the next step 204, from the position data of the regions of interest on the first image and the regions of interest on the second image determined to "have correlation", the range of positions are estimated in the Z plane (the vertical plane in the present exemplary embodiment) of these regions of interest. Then, from the estimated range of the positions in the Z plane, the range of positions of the regions of interest determined to "have correlation" in the above first image and the above second image are estimated on the image (referred to below as the third image) obtained by radiation irradiation when the position of the radiation irradiation section 24 was at $P_{k-1}$ ($2 \leq K \leq N-2$) and on the image (referred to below as the fourth image) obtained by radiation irradiation when the position of the radiation irradiation section 24 was at position $P_{k+2}$ ($2 \leq K \leq N-2$). In cases where there is a region of interest present in the estimated range of positions on the third image and the fourth image, the region of interest determined to "have correlation" between the first image and the second image is confirmed as "being correlated". Namely, the loci of attention expressed by the region of interest that were determined to "have correlation" between the first image and the second image are applied with a preliminarily association with each other. Note that configuration may be made such that in cases where there is a one-to-many relationship, "being correlated" may be confirmed for the regions of interest determined to have correlation" between the first image and the second image if there is a region of interest present in the estimated range of positions in the third image and the fourth image, and in cases where there is a one-to-one relationship, "being correlated" may be confirmed without performing step 204.

In the next step 206, determination is made as to whether or not there is a combination of $P_k$ ($2 \leq K \leq N-2$) and $P_{k+1}$ not yet selected in step 200. When positive determination is made at step 206, processing returns to above step 200, and the yet to be selected combination of $P_k$ ($2 \leq K \leq N-2$) and $P_{k+1}$ is selected. However, processing proceeds to step 208 when negative determination is made at step 206.

At step 208, verification is made as to whether or not the Z axis coordinates of the "have correlation" regions of interest are within a specific tolerance range, with determination made that they are the same region of interest if found to be within this tolerance range. The locus of attention expressed by the regions of interest determined to be the same region of interest are confirmed as associated with each other. When the Z axis coordinates are split into two and not within the tolerance range, then determination is that they are separated regions of interest, and the preliminary association is removed.

At the next step 210, as shown in FIG. 9, each of the loci of attention that have been associated by the above steps 200 to 208 (or more specifically confirmed as associated) are formed into a chart 99 showing whether or not they are present in each of the N frames of images, and stored in the HDD 66, and the chart generation processing is ended. Note that in the example in FIG. 9, the chart 99 shows whether or not each of the associated loci of attention A to H are present in each of the images from the $1^{st}$ image to the $N^{th}$ image. Here "PRESENT" indicates that the locus of attention is present in the corresponding image, and "ABSENT" indicates that the locus of attention is not present in the corresponding image. The example in FIG. 9 shows that the locus of attention A is present in the $1^{st}$ image, but the locus of attention C is not present in the $1^{st}$ image.

Note that while steps 200 to 208 cover processing for associating the locus of attention in each of the images, there is no limitation to the processing of the above steps 200 to 208, and configuration may be made such that processing is performed for associating the locus of attention between each of the images prior to generating the chart 99 in step 210. For example, since two radiographic images are imaged of the breast N from different respective angles, corresponding regions of interest are included. Consequently, for example, by taking as a reference position the position where the region of interest is present in one of the radiographic images out of the two radiographic images, the corresponding point can be derived by searching from the reference position in the other radiographic image and matching in a region determined according to the thickness D between the press plate 26 and the imaging face 20. In order to derive the association relationships with good precision, for example, a region of interest of one of the radiographic images may be searched for in the other radiographic image, and a region of interest in the other radiographic image may be searched for in the first radiographic image, such that corresponding points in both are found. A region of interest in two radiographic images can be identified by a particular position (such as, for example, a very small calcified cluster) in the breast N using computer aided detection (CAD), and the association relationship can be derived for the identified region of interest.

Explanation now returns to FIG. 5. First image selection processing is executed in the next step 104. FIG. 10 shows a flow chart of the first image selection processing executed at step 104. According to the first image selection processing, out of combinations of the images from the N frames of image, the combination with the minimum number of frames of images having all of the loci of attention expressed by the detected regions of interest (regions of attention) are selected as images for displaying on the display device 80.

First, at step 300, the image including the greatest number of loci of attention is selected from the N frames of images.

At the next step 302, any loci of attention not included in the already selected images are identified, and the image with the greatest number of these identified loci of attention is selected.

At the next step 304, determination is made as to whether or not the number of loci of attention identified at above step 302 is 0. When determination that it is not 0 is made at step 304 (namely that there is 1 or more) then processing returns to step 302. However, when determined to be 0 at step 304, processing proceeds to the next step 306, and the images selected at step 300 and step 302 are determined as images for displaying on the display device 80, thereby concluding the first image selection processing. From the chart 99 shown in FIG. 9, as an example, the "1$^{st}$ image", the "M$^{th}$ image", and the "N–1$^{th}$ image" are selected at step 300 and step 302, and these images are determined as the images for displaying on the display device 80.

Then, in step 106, control is made such that the images selected in step 300 and step 302 in the above first image selection processing are displayed on the display device 80. Accordingly, since the minimum number of images are displayed in order to display all of the loci of attention, images are displayed such that efficient interpretation can be made, while suppressing loci of attention from being overlooked.

Second Exemplary Embodiment

Figure 11:
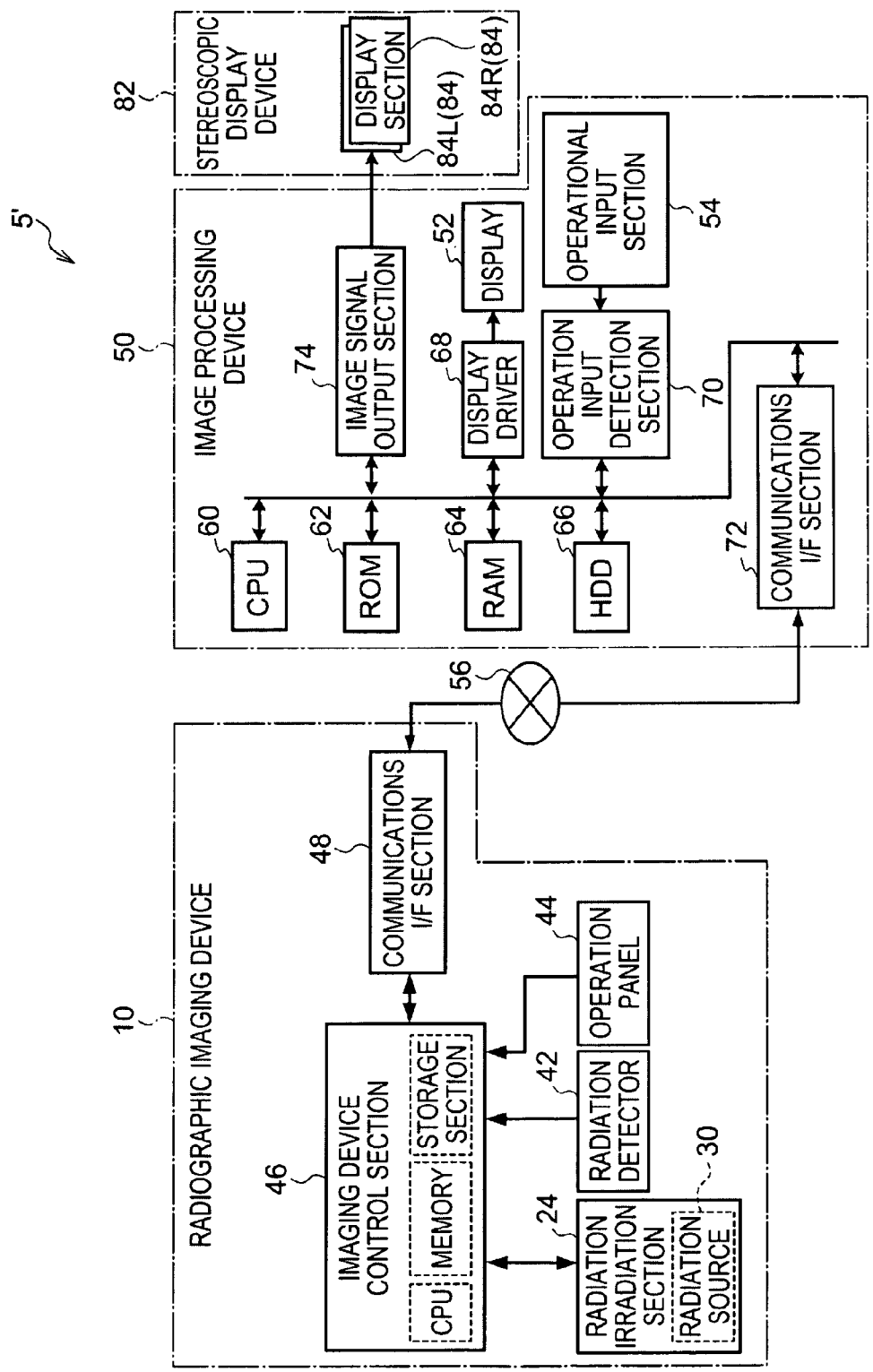
FIG. 11 is a block diagram showing a configuration of a radiographic imaging system according to a second exemplary embodiment

Explanation now follows regarding a second exemplary embodiment. Similar configuration and processing to that of the first exemplary embodiment is allocated the same reference numerals and further explanation thereof is omitted. The display device 80 is employed as the display section in the first exemplary embodiment, however, in the radiographic image display system 5' of the present exemplary embodiment, as shown in FIG. 11, a stereoscopic display device 82 is employed as the display section. In the first exemplary embodiment, the CPU 60 of the image processing device 50 receives specific instructions and executes the first display control processing, however in the present exemplary embodiment, the CPU 60 receives specific instructions and executes second display control processing.

Figure 12:
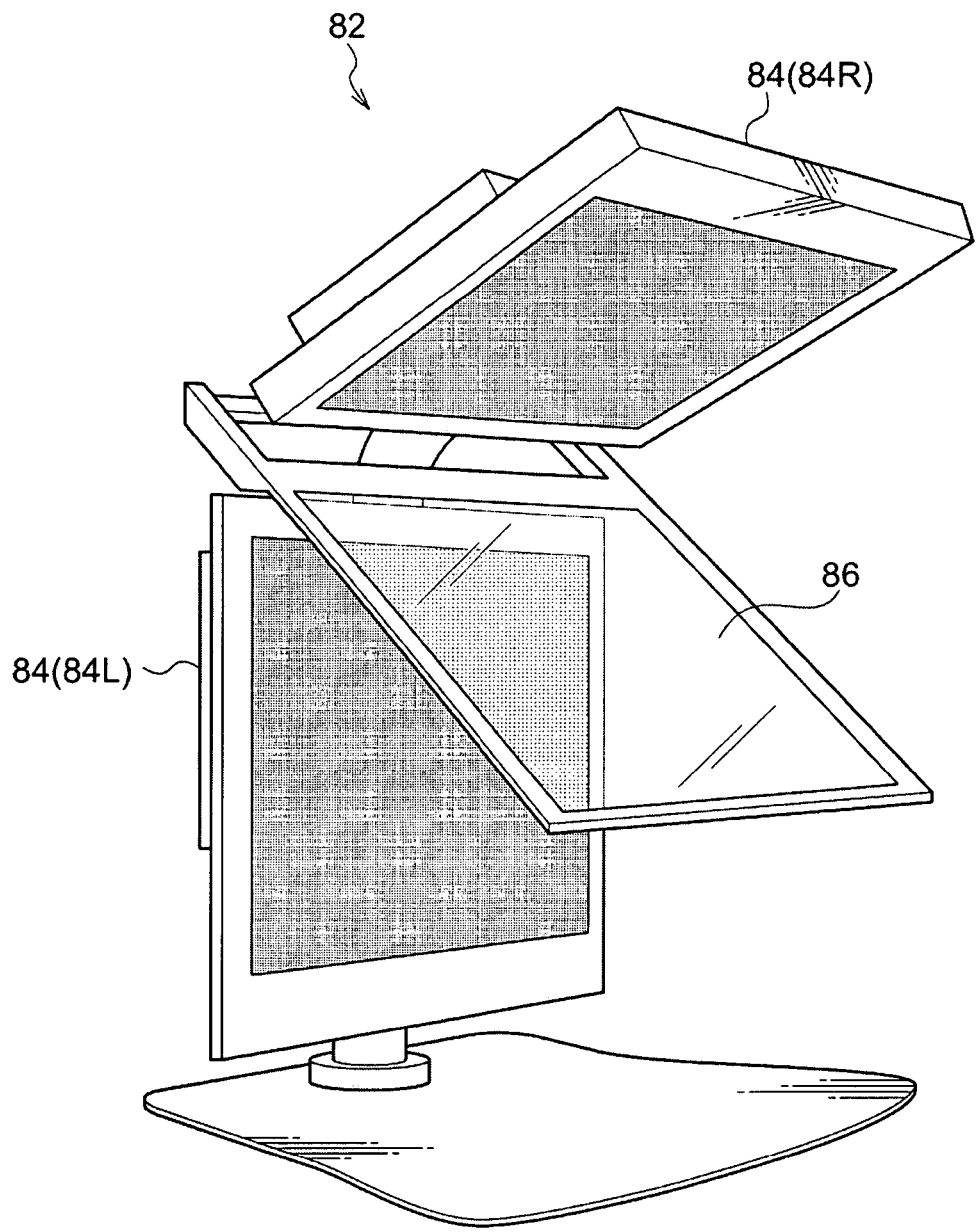
FIG. 12 is a block diagram showing a configuration of a stereoscopic display device according to the second exemplary embodiment.

FIG. 12 shows an example of a configuration of the stereoscopic display device 82 according to the present exemplary embodiment.

As shown in FIG. 12, the stereoscopic display device 82 has two display sections 84 disposed next to each other, one above the other, with the upper of the display sections 84 fixed at an angle to the other. The two display sections 84 have display light with mutually orthogonal polarization directions, with the upper display section 84 configuring a display section 84R for displaying an image for right-eye-use, and the lower display section 84 configuring a display section 84L for displaying an image for left-eye-use. A beam splitter mirror 86 is provided between the display sections 84L, 84R. The display light from the display section 84L is transmitted through the beam splitter mirror 86, and the display light from the display section 84R is reflected by the beam splitter mirror 86. The angle of the beam splitter mirror 86 is adjusted and fixed such that the image displayed by the display section 84L and the image displayed by the display section 84R are superimposed on each other when an observer views the stereoscopic display device 82 from the front.

Figure 13:
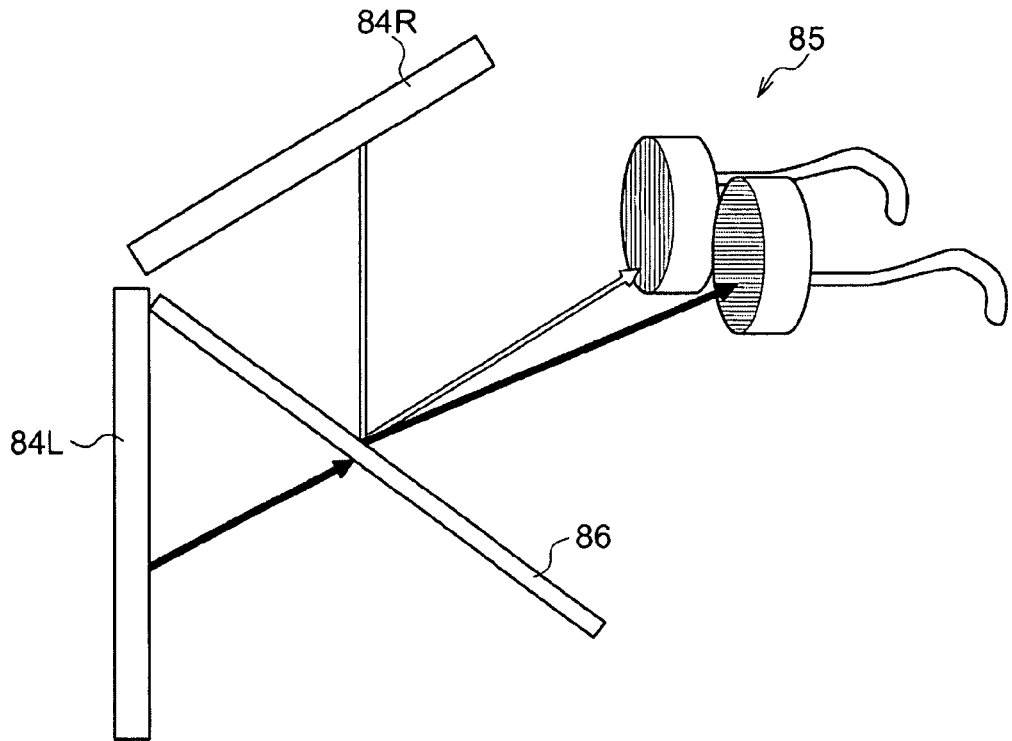
FIG. 13 is a block diagram showing a configuration of a stereoscopic display device according to the second exemplary embodiment.

An observer, as shown in FIG. 13, can separately view the image displayed by the display section 84L and the image displayed by the display section 84R with the left eye and the right eye, respectively, by viewing the stereoscopic display device 82 while wearing polarized glasses 85 with mutually orthogonal polarization directions in the right lens and the left lens.

Figure 14:
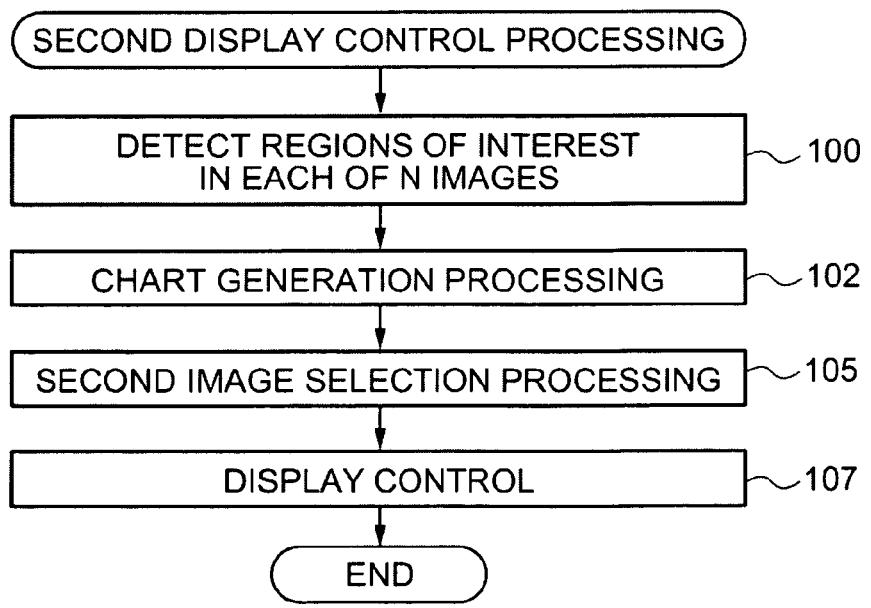
FIG. 14 is a flow chart showing a flow of second display control processing according to the second exemplary embodiment.

FIG. 14 shows a flow chart of a flow of the second display control processing of a second display control processing program executed by the CPU 60 on receipt of a specific instruction. Such a program is, for example, pre-stored in a specific region of the ROM 62.

Regarding the processing at step 100 and step 102, further explanation is omitted since it is similar to the processing of the first exemplary embodiment described above.

Figure 15:
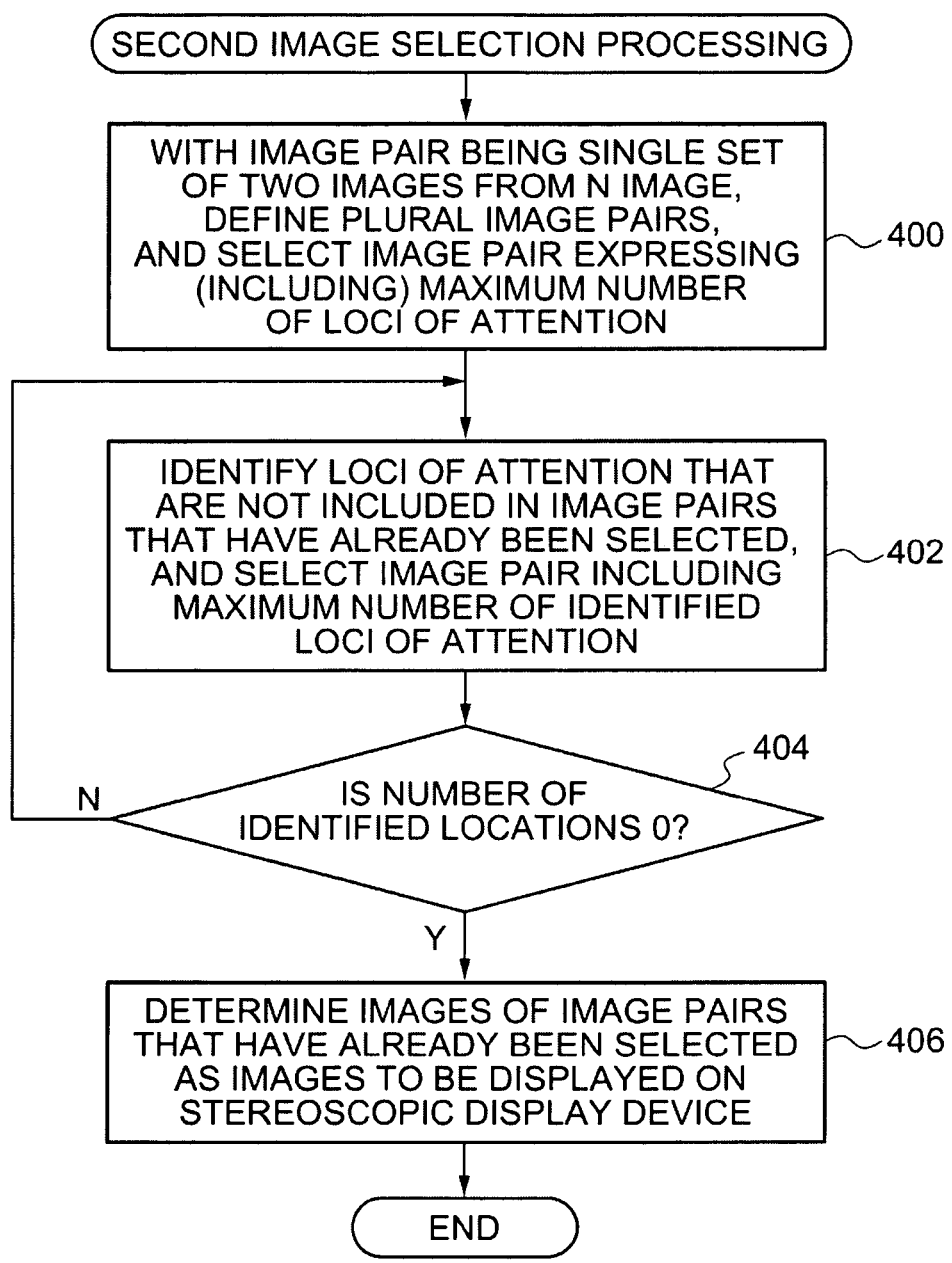
FIG. 15 is a flow chart showing a flow of second image selection processing according to the second exemplary embodiment.

The second image selection processing is executed in step 105 following after step 102. FIG. 15 shows a flow chart of the second image selection processing executed in step 105. By the second image selection processing, in cases where there are plural sets of pairs of images (image pairs), a pair of images being a single set of two images from the N frames of images, image pairs are selected from the N frames of images as images for displaying on the stereoscopic display device 82 such that the minimum number of image pairs images are selected having all the loci of attention expressed by the detected regions of interest (regions of attention).

First, at step 400, with an image pair being a single set of two frames of images from the N frames of images, plural sets are determined, and the image pair expressing (including) the maximum number of loci of attention is selected. Note that in the present exemplary embodiment, each of the image pairs is two frames of images obtained by radiating radiation with the radiation irradiation section 24 from different positions that are at a specific parallactic angle to each other. Namely, each of the image pairs is two frames of images acquired by imaging with the radiographic imaging device 10 at different imaging positions that form a specific parallactic angle to each other.

In the next step 402, any loci of attention not included in the image pairs already selected are identified, and the image pair having the maximum number of identified loci of attention is selected.

In the next step 404, determination is made as to whether or not the number of identified loci of attention at above step 402 is 0. When determined not to be 0 at step 404 (namely where 1 or more exists) processing returns to above step 402. However, when determined to be 0 at step 404, at the next step 406, the images of the image pairs selected at above step 400 and step 402 are determined as the images for display on the stereoscopic display device 82, and the second image selection processing is ended. FIG. 16 shows a chart 99' generated at step 102 of the present exemplary embodiment. In the example of the chart 99', as an example, the "image pair of the 1$^{st}$ image and the 2$^{nd}$ image", "image pair of the M$^{th}$ image and the M+1$^{th}$ image" and "image pair of the N–1$^{th}$ image and the N$^{th}$ image" are selected, and determined as the images of the image pairs to be displayed as images on the stereoscopic display device 82.

Then in step 107, the stereoscopic display device 82 is controlled such that images of each of the image pairs selected by the second image selection processing at step 400 and step 402 are displayed in sequence. Accordingly, since the minimum number of images are displayed in order to display all of the region of interest, images are displayed such that efficient interpretation can be made, while suppressing regions of interest from being overlooked. Furthermore, since 3-dimensional display is made, time is saved when considering the three dimensional image of the breast N as a whole, and even more efficient interpretation can be made, while suppressing regions of interest being overlooked.

Note that in the above exemplary embodiments, explanation has been given of cases applied to radiographic images imaged by mammography, however the present invention is not limited thereto, and application may be made to other radiographic imaging devices.

Furthermore, in the above exemplary embodiments, explanation has been given of cases in which the digital image data expressing radiographic images is directly obtained by the radiation detector 42, however the present invention is not limited thereto. For example, configuration may be made in which radiation is irradiated onto a cassette installed with an imaging plate or X-ray film or the like, and digital image data is obtained by reading in the imaging plate or the X-ray film installed in the cassette.

Note also that the configurations of the radiographic imaging device 10, the display device 80, and the stereoscopic display device 82 in the radiographic image display systems 5, 5' explained in the above exemplary embodiments are only examples thereof, and obviously modification is possible thereto according to the circumstances, within a scope not departing from the spirit of the present invention.

Further, the foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The exemplary embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An image display system comprising:
   an image acquisition section that acquires a specific number of images of an imaging subject by imaging with an imaging section from different respective imaging positions;
   a detection section that detects regions of attention expressing specific loci of attention in each of the specific number of images acquired by the image acquisition section; and
   a selection section that determines, from the specific number of images, a combination of images having a minimum number of images having all of the loci of attention expressed by the regions of attention detected by the detection section, and selects the determined combination of images as images to be displayed on a display section.

2. The image display system of claim 1, further comprising:
   an association application section that, between the images, applies associations to regions of attention that express a same locus of attention, based on an imaging position of the imaging section in each of the specific number of images and a position of the region of attention detected in each of the images; and wherein,
   the selection section selects, from the combinations of the images, the combination of images for display as images on the display section, the combination of images having the minimum number of images having all of the loci of attention expressed by the regions of attention detected by the detection section in the specific number of images, based on the associations applied by the association application section to the regions of attention expressing the same locus of attention.

3. An image display system comprising:
   an image acquisition section that acquires a specific number of images of an imaging subject by imaging with an imaging section from different respective imaging positions;
   a detection section that detects regions of attention expressing specific loci of attention in each of the specific number of images acquired by the image acquisition section; and
   a selection section that, in cases where there are a plurality of sets of image pairs determined, each image pair being a single set of two images in the specific number of images imaged by the imaging section, determines, from the specific number of images, a combination of image pairs having a minimum number of the image pairs having all of the loci of attention expressed by the regions of attention detected by the detection section, and selects the determined combination of image pairs as images to be displayed on a display section.

4. The image display system of claim 3, further comprising:
   an association application section that, between the images, applies associations to regions of attention that express a same locus of attention, based on an imaging position of the imaging section in each of the specific number of images and a position of the region of attention detected in each of the images; and wherein,
   the selection section selects, from the combinations of the image pairs, the combination of image pairs for display as images on the display section, the combination of image pairs having the minimum number of the image pairs having all of the loci of attention expressed by the regions of attention detected by the detection section in the specific number of images, based on the associations applied by the association application section to the regions of attention expressing the same locus of attention.

5. The image display system of claim 3, wherein:
   each of the image pairs is two images acquired by imaging with the imaging section at different imaging positions that are at a specific parallactic angle to each other; and
   the display section displays images of each of the image pairs in the selected combination as a three-dimensional image.

* * * * *